United States Patent [19]

Kropfhammer

[11] E Re. 29,613

[45] Reissued Apr. 18, 1978

[54] INHALER APPARATUS

[76] Inventor: Georg Kropfhammer, Seebruck, Germany

[21] Appl. No.: 786,475

[22] Filed: Apr. 11, 1977

Related U.S. Patent Documents

Reissue of:

[64] Patent No.: 3,964,478
Issued: Jun. 22, 1976
Appl. No.: 489,898
Filed: Jul. 19, 1974

[30] Foreign Application Priority Data

Jul. 19, 1973 Germany ..... 2336879
Jun. 20, 1974 Germany ..... 2429508

[51] Int. Cl.[2] ..... A61M 16/00

[52] U.S. Cl. ..... 128/203; 194/DIG. 18; 222/70; 194/4 R; 194/5

[58] Field of Search ..... 128/203, 208, 185, 172, 128/140 R, 188, 145.8, 142, 142.3, 146–146.6, 147, 2.08; 194/4 R, 5 R, 4 D, 4 F, 4 G, DIG. 18; 222/70 R

[56] References Cited

U.S. PATENT DOCUMENTS

| | | | |
|---|---|---|---|
| 2,122,897 | 7/1938 | Straw | 128/203 |
| 2,166,872 | 7/1939 | Mayers | 128/203 |
| 2,794,869 | 6/1957 | Noregaard | 194/4 R |
| 2,831,607 | 4/1958 | Berndt | 128/185 |
| 2,855,926 | 10/1958 | Koppelman | 128/203 |
| 3,042,035 | 7/1962 | Coanda | 128/146 |
| 3,073,301 | 1/1963 | Hay et al. | 128/203 |
| 3,390,676 | 7/1968 | Warnck et al. | 128/203 |
| 3,685,625 | 8/1972 | Loewy | 194/4 R |
| 3,747,598 | 7/1973 | Cowans | 128/212 |

*Primary Examiner*—Robert W. Michell
*Assistant Examiner*—Henry J. Recla
*Attorney, Agent, or Firm*—Hopgood, Calimafde, Kalil, Blaustein and Lieberman

[57] ABSTRACT

An inhaler apparatus includes a housing which encloses a gas source, a gas applicator, a feed hose which connects the gas source and applicator and a valve for controlling the flow of gas from the source to the applicator. The housing includes a lid which provides access to the applicator when open and prevents access when closed. Locking means are provided to hold the lid in the closed position and means such as an insertable strip or key are provided to disengage the locking means and provide access to the applicator.

22 Claims, 21 Drawing Figures

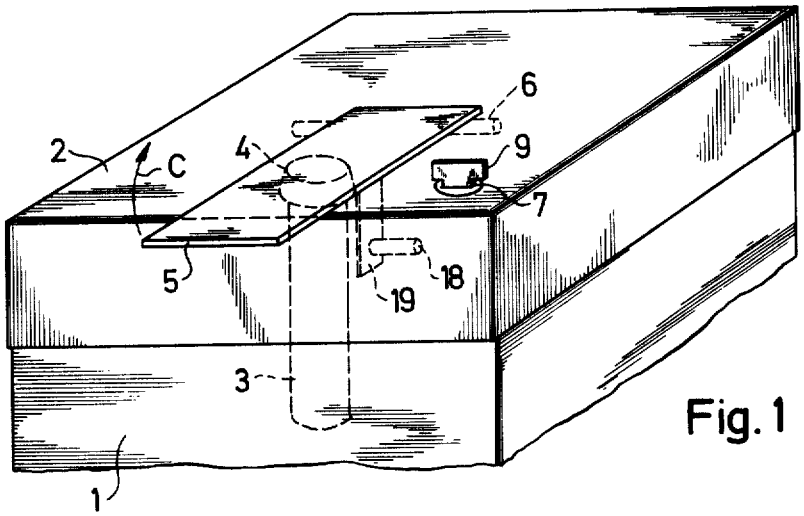
Fig. 1
Fig. 2
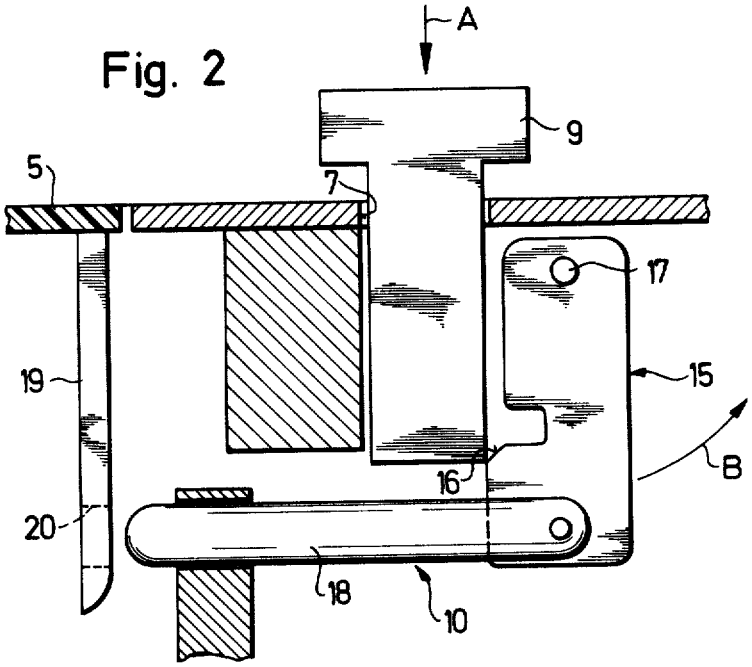

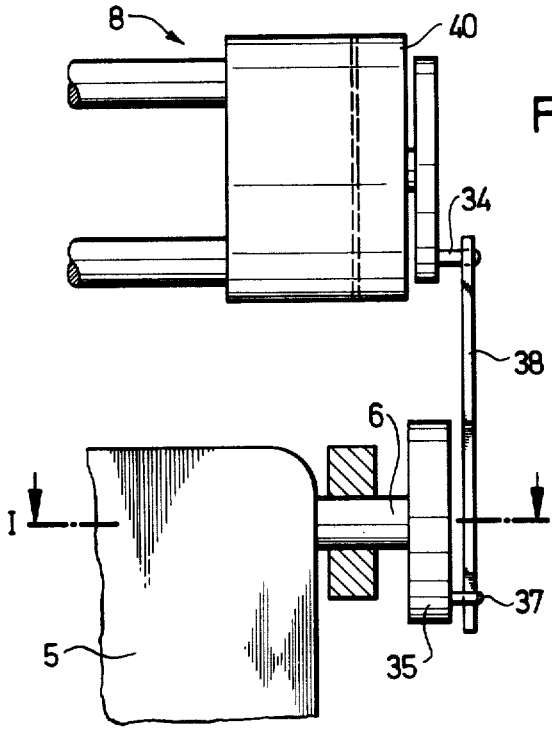
Fig. 3
Fig. 4
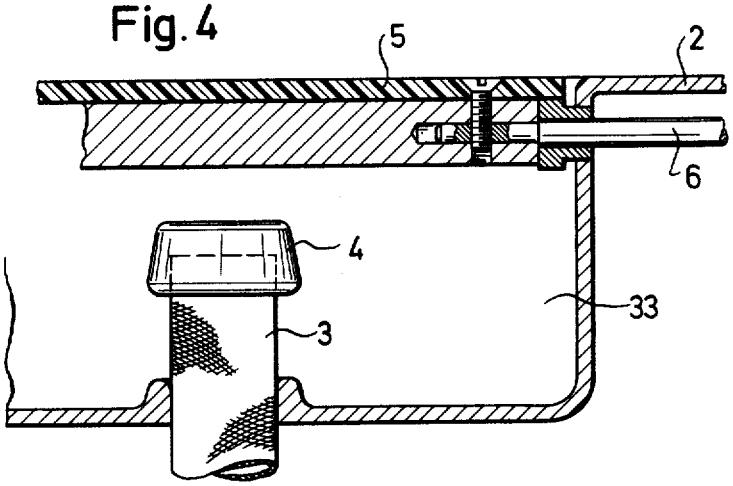

INHALER APPARATUS

Matter enclosed in heavy brackets [ ] appears in the original patent but forms no part of this reissue specification; matter printed in italics indicates the additions made by reissue.

BACKGROUND OF THE INVENTION

The present invention relates to an inhaler comprising a gas source which stores or generates gases, vapours and/or aerosols to be inhaled; an attachment such as an inhaling mask, mouth piece, nose piece or cannula; a feed hose for feeding the gases to the attachment; a shut-off device such as a valve, for shutting off the supply of gas and the like; and a housing for the gas source which can be closed by means of a lid. If desired, a device for moistening the gases can also be included.

Inhalers of this type are already known such as that described in LUEGER, Lexikon der Technik, Vol. 13, 1968, at pages 468 and 469. Inhalers of this type are used for the administration of gases, especially oxygen, aerosols and vapours. The gas source can be, for example, an oxygen cylinder containing pure oxygen under high pressure which, after the valve has been opened, is reduced to a lower working pressure in a connected pressure reducing and is inhaled either as pure oxygen or as an oxygen and air mixture. If necessary, the gases, aerosols or the like, can be moistened by the moistening device. The moistening device can be a group of fine-meshed sieves which cause moisture in the exhaled gas to condense and thus moisten the gas to be inhaled.

Known inhalers which include oxygen tents and incubators normally can only be operated by trained specialists such as doctors or nurses and hence cannot be used in places where such specialists are not available. Oxygen deficiency often exists in places where the air contains an increased proportion of carbon monoxide, nitrogen or other noxious substances, and it would be desirable to have an apparatus which can be operated economically and by a laymen to eliminate such oxygen deficient condition. Lack of oxygen can result in tiredness, unwillingness to work, lack of concentration, irritability, and breathing difficulties, which can in turn lead to accidents at work and at the very least will considerably impair the health and the working capacity of persons staying in such an environment. Traffic police and road workers, for instance, work in areas contaminated by exhaust gases. Employees in some factories and even offices where the air quality gradually deteriorates frequently do not even recognize the risks to their health and working capacity.

It is the object of the invention to provide an inhaler which is simple to operate and which a laymen can operate and which will prevent an excessive consumption of the inhalant with resulting rapid exhaustion of the gas source. The inventive device also provides protection against the unauthorized removal of inhalant.

SUMMARY OF THE INVENTION

An inhaler includes a housing surrounding a gas source, an applicator for gas, a feed hose connected between the gas source and the applicator and valve means for controlling the gas flow from the source to the applicator. The housing includes a movable lid which in an open position provides access to the applicator which can be withdrawn from the housing. Locking means are provided which when engaged hold the lid in a closed position preventing access to the applicator. An unlocking element is provided which disengages the locking means to permit the lid to open and provide access to the applicator.

If desired the valve means may be connected to the lid or locking means so that the valve means will block gas flow to the applicator when the lid is closed and will permit gas flow when the lid is opened. This provides automatic control of the flow of gas by the position of the lid and will block the gas flow when the lid is closed to prevent wasting the gas. If desired, the degree of opening of the valve means and thus the amount of gas supplied to the applicator per unit time likewise be controlled by the position of the lid.

The locking means can include a lever which is movable by the unlocking element and is functional connected to a locking element which locks the lid in a predetermined position. The locking element or alternatively the valve means may be provided with a timer which shuts the valve means a predetermined adjustable period of time after the lid has been released. This will prevent the unnecessary flow of gas even if the lid has not been restored to its closed position by closing the valve means. Since a relatively short period of oxygen inhalation will suffice to compensate for oxygen deficiency in the blood, a short-duration timer may be used with the inventive structure to return the valve means to its locking position.

The timer may be connected to the lid or to a lever member via a coupling device so that it will be engaged only when the unlocking element releases a blocking member.

According to a further development of the invention, the inhaler can be provided with means for cancelling the unlocking element after release of the shut-off valve. This cancelling element will render the unlocking element useless after a predetermined number of uses. It would therefore be possible to sell unlocking elements which can be cancelled and to obtain in this way an adequate price for the installation and maintenance of the inhaler and the supply of inhalants.

The applicator and the part of the feed hose adjacent to the applicator should be stored in a holding device arranged inside the lid or in a housing compartment behind the lid when the lid is in a closed position. When the lid is opened, the attachment will then be at once available and when the operator has finished using the inhaler, a storage place is readily available. The feed hose should be elastically flexible and may also be extendable. It is expedient for the feed hose to retract automatically into the housing compartment when the applicator is returned to the holder.

Since the inhaler according to the invention can be used by a number of persons whose state of health is often not foreseeable, in another feature of the invention the applicator is joined to the feed hose or to a coupling element connected to the feed hose in such a way that it can easily be detached and replaced. The applicator can then be replaced by another applicator after each application in order to obviate possible infection. It is, therefore, expedient to design the applicator as a disposable element which will be destroyed after having been used once. Such applicators can be made of deep-drawn synthetic plastics.

The applicator can include a frustum-shaped outer wall and a perforated indented central partition which can be fitted easily to the end of the feed hose or a holder. Such simple applicators serving as inhaling masks must not involve high production costs since they are to be disposable.

A moistening device can be inserted between the gas source and the feed hose. For many cases, it is also advisable to add aroma substance to the inhalant. For this purpose, it is expedient to arrange an expansion chamber between the gas source and the feed hose into which chamber such substances can be placed.

If desired, a single inhaler housing can include several lids with several applicators and feed hoses stored within the housing. A single housing then provides several separately accessible, separately sealed inhalers.

BRIEF DESCRIPTION OF THE DRAWINGS

Embodiments of the invention are explained in the following with reference to the drawings wherein similar parts are designated by the same reference number.

FIG. 1 is a partially isometric illustration of the inhaler seen from the outside;

FIG. 2 is a vertical section through the part of the apparatus housing the blocking aggregate of FIG. 1;

FIG. 3 is a view of the timer and the elements by which it is actuated;

FIG. 4 is a vertical section along the line I—I of FIG. 3;

DESCRIPTION OF THE INVENTION

Figure 5:
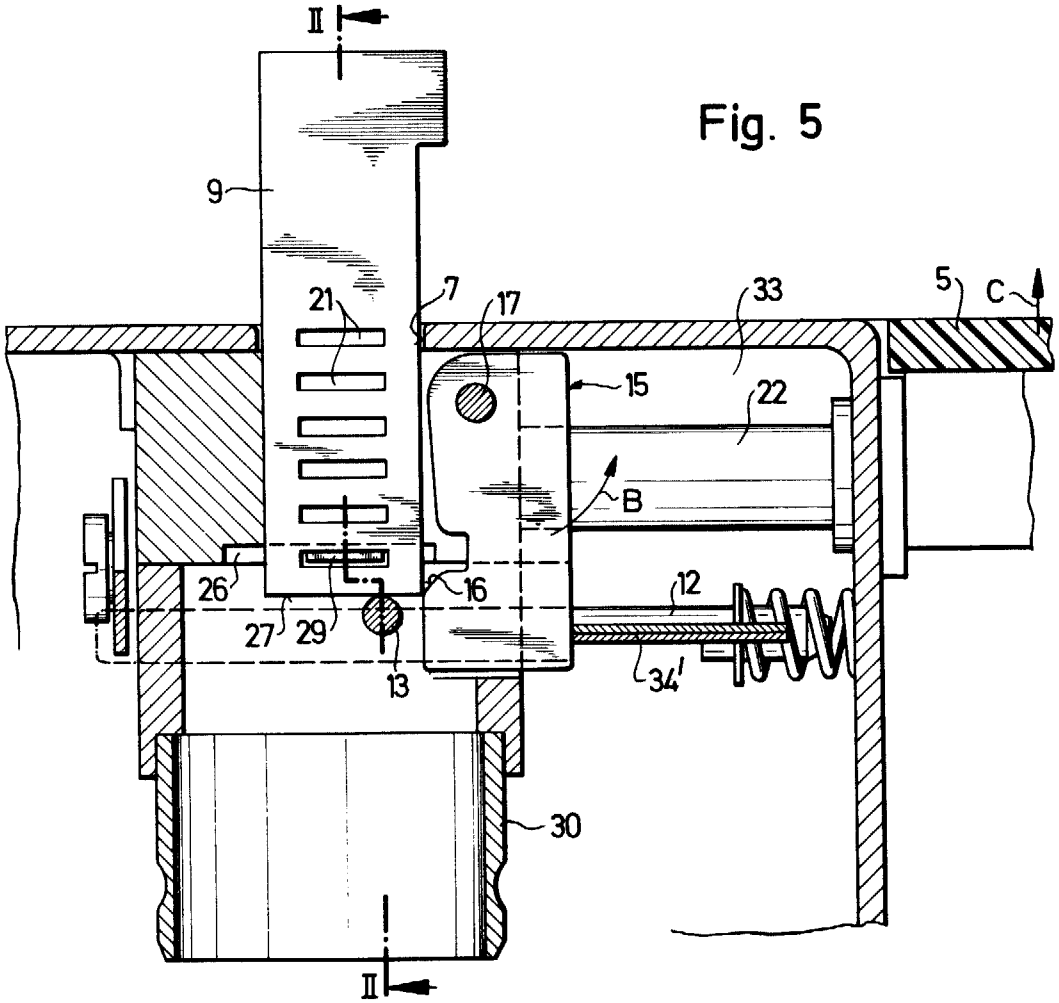
FIG. 5 is a sectional view of a part of a further embodiment of the invention.

The inhaler according to FIG. 1 includes a substantially square housing consisting of a base 1 and a top 2. One or more high-pressure steel cylinders such as 36 in FIG. 15 containing liquid oxygen are arranged in the interior of the base 1 as gas sources. The outlet conduit of these oxygen cylinders is connected through a pressure reducing valve into an expansion vessel and, finally, via a flexible feed hose 3 to an applicator such as a mouthpiece or an inhaling mask which may be slipped over the mouth and nose. The applicator, which is replaceable is held against the mouth or the nose to permit the inhaling of oxygen. The feed nose 3 can be partially extendable from the housing 1, 2. When the apparatus is not in use, the free end of the feed hose 3 with the applicator 4 are housed in a niche-like compartment 33 of the housing 1, 2 which compartment is covered by the lid 5. This lid 5 which may also be shaped like a hood can be swivelled together with an attached horizontal shaft 6 which is mounted in the top 2 of the housing. The shaft 6 is fixedly connected to the lid 5 by means of screws. The shaft 6 co-operates with the valve 8 in a manner to be described below.

The device is so designed that the oxygen supply to the hose 3 and therefore to the applicator 4 is interrupted by at least one valve 8 of FIG. 3 which serves as a shut-off valve, as long as the lid 5 is closed as shown in FIG. 1. The lid 5 also cooperates with a locking device 10 which serves to hold the lid 5 in its closed position so that unauthorized persons have no access to the applicator 4 or to the oxygen.

The locking device 10 for the lid 5 is unlocked by an unlocking element 9 which may be for example a T-shaped strip of a rigid material such as a synthetic plastic as shown in FIG. 2. Other devices such as keys or coin-type objects are also usable as unlocking elements. If desired the strip 9 can be provided with coding means, for example, in the form of apertures or an irregular cross sectional area, in order to prevent as far as possible imitations or forgeries.

When the unlocking element 9 is inserted in the direction of the arrow A in FIG. 2 into a slot-shaped aperture 7 in the top 2 of the housing, a rocker arm 15 moves in the direction of the arrow B, because the lower edge of the strip 9 presses against the inclined abutting surface 16 of arm 15. The rocker arm 15 then swivels around a shaft 17 attached to the housing. One end of rod member 18 is attached to arm 15 so that the rod 18 moves to the right in FIG. 2 as strip 9 is depressed. The other end of the rod 18 cooperates with a lug 19 which is secured to the lid 5 so that the rod is moved into and out of the aperture 20 in lug 19 depending on whether or not unlocking element 9 is pressed against surface 16 of arm 15.

The lid 5 can thus only be swivelled in the direction of the arrow C into an open position when the correct unlocking element 9 has been inserted in the associated slot 7 moving rod 18 out of lug aperture 20 and freeing lug 19 and the attached lid 5 to move upward.

In response to the swivelling motion of the lid 5, the shut-off valve 8 of FIG. 3 is opened by purely mechanical means permitting oxygen to flow to the applicator 4. For this purpose the shaft 6 is fixedly connected to a disc 35. A projecting member 37 projects from and is eccentrically arranged on disc 35. Projecting member 37 engages one end of a lever-shaped connecting element 38. A bolt 34 engages the connecting element 38 at the other end. This bolt 34 forms the winding pin for a timer 40 which controls the shut-off valve 8, by means of an actuating member. A detachable coupling is provided which causes the driving connection to be disengaged after the winding motion so that the timer 40 can freely return to its unwound position. The timer 40 is arranged to keep the valve 8 closed when the timer is unwound and to open the valve 8 after the winding motion and keeps it open until the timer returns to its unwound position permitting the flow of oxygen to the applicator 4 during a period determined by the timer 40. Consequently, swivelling of the lid 5 in the direction of the arrow C winds the timer 40 with the aid of the connecting elements 6, 35, 37 and 38. When the predetermined time to which the timer can be set has lapsed, the valve 8 is shut again. The hose 3 is then returned to the housing compartment 33 where it is stored and the lid 5 is closed.

Figure 6:
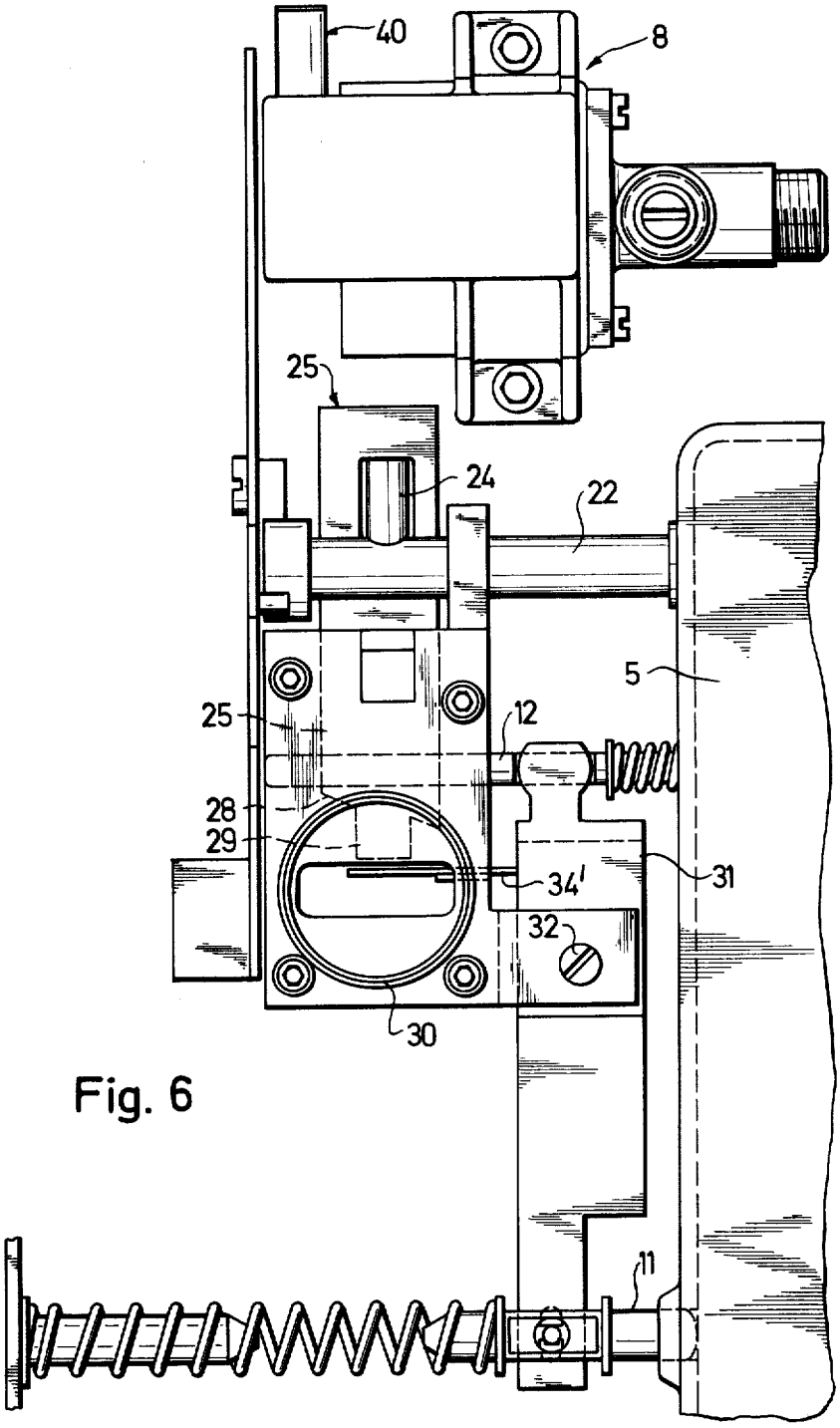
FIG. 6 is a view of the device of FIG. 5 seen from below.
Figure 7:
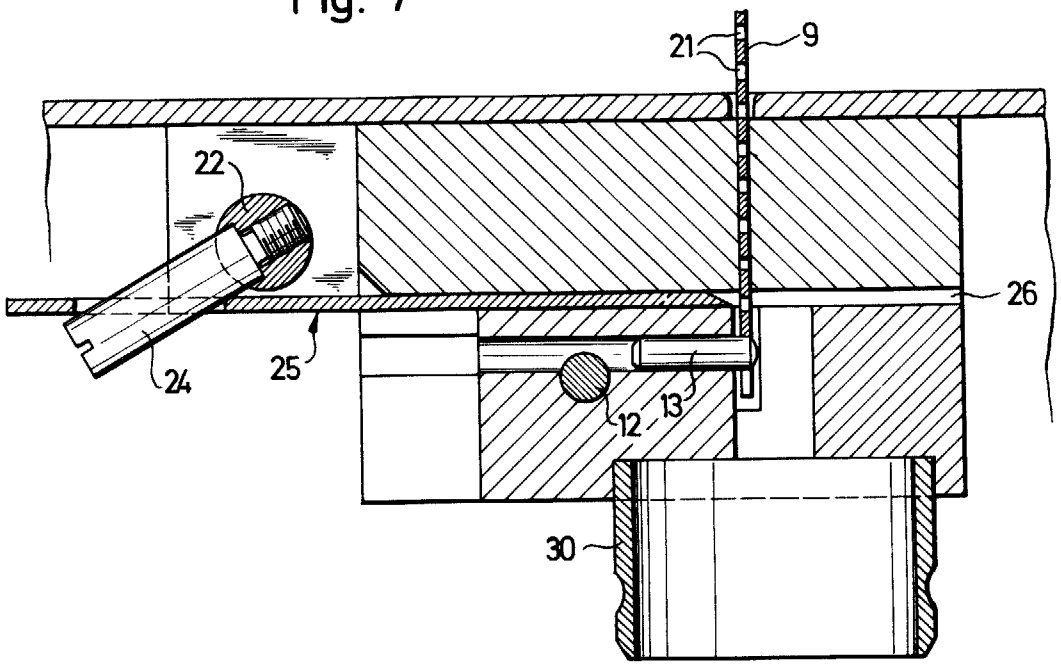
FIG. 7 is a section along the line II—II of FIG. 5.

A second embodiment of the invention shown in FIGS. 5 to 7 likewise serves for supplying authorized persons with oxygen for inhaling purposes. An insertable of rigid synthetic plastic material 9 is utilized as an unlocking element 9. This strip 9 includes several slot-shaped apertures 21 arranged longitudinally along the strip. Each time the strip 9 is utilized to open lid 5 a pice is cut off from the strip and it is thus partially cancelled.

When the unlocking element 9 is introduced into the aperture 7 of top 2 the rocker arm 15 is swivelled about shaft 17 in the direction of the arrow B and moves a bolt 34 against a lever 31 shown in FIG. 6. Lever 31 in turn swivels around a shaft 32. One end of this lever 31 cooperates with a locking bolt 11 causing bolt 11 to move to the right as seen in FIG. 6 thereby releasing lid 5. The other end of lever 31 abuts an unlocking pin 12 by means of which a mechanical coupling can be established via intermediate mechanical elements between the swivelling lid 5 and a timer 40 which actuates the shut-off valve 8 permitting the flow of gas.

The depth to which the unlocking element 9 is inserted is limited by a pin 13. When the lower edge 27 of element 9 abuts this pin 13, one lower corner of the strip 9 is pressing against the inclined abutting surface 16 of the arm 15 and the lock of the lid provided by the locking bolt 11 is released. The lid 5 can then be swivelled upwards in the direction of the arrow C in FIG. 5 rotating a shaft 22 which is mounted in the housing compartment 33. A bolt 24 projects in a radial direction from shaft 22 so that it cooperates with a flat knife 25 which acts to sever a piece of the unlocking element 9. The knife 25 is guided in a slot 26 as seen in FIG. 7 in such a way that it moves parallel to its longitudinal direction. The blade 28 of knife 25 is bevelled so that the cutting process extends over a predetermined distance. A flat tongue 29 projects from the central part of the blade 28 to act as guide element which engages the apertures 21 of element 9. The apertures 21 of unlocking element 9 are thus accurately aligned for the subsequent cutting operation and the strip 9 is prevented from being pulled out again after the lid 5 has been unlocked.

When the lid 5 and hence the shaft 22 are swivelled further, the blade 28 will pass through strip 9 cutting off a piece from the end of the strip. The cutting line is preferably arranged to be parallel to the upper edge of the aperture 21 concerned. The rotation of the shaft 22 also acts via intermediate members which are not described in detail but are similar to the arrangement described above for the first embodiment to release the valve 8 for the gas supply to the hose 3 and the applicator 4. The waste piece cut off from the stip 9 falls through a pipe 30 into a container or bag.

A third embodiment as shown in FIGS. 8 through 11 can be used for the dosed administration of a gas, such as oxygen, and includes an inserting or cashing device. The term "inserting or cashing device" is to be understood in the widest sense and includes coin collecting means as well as devices which accept chips or other insertable organs of any shape. It will also include key-operated devices.

Figure 9:
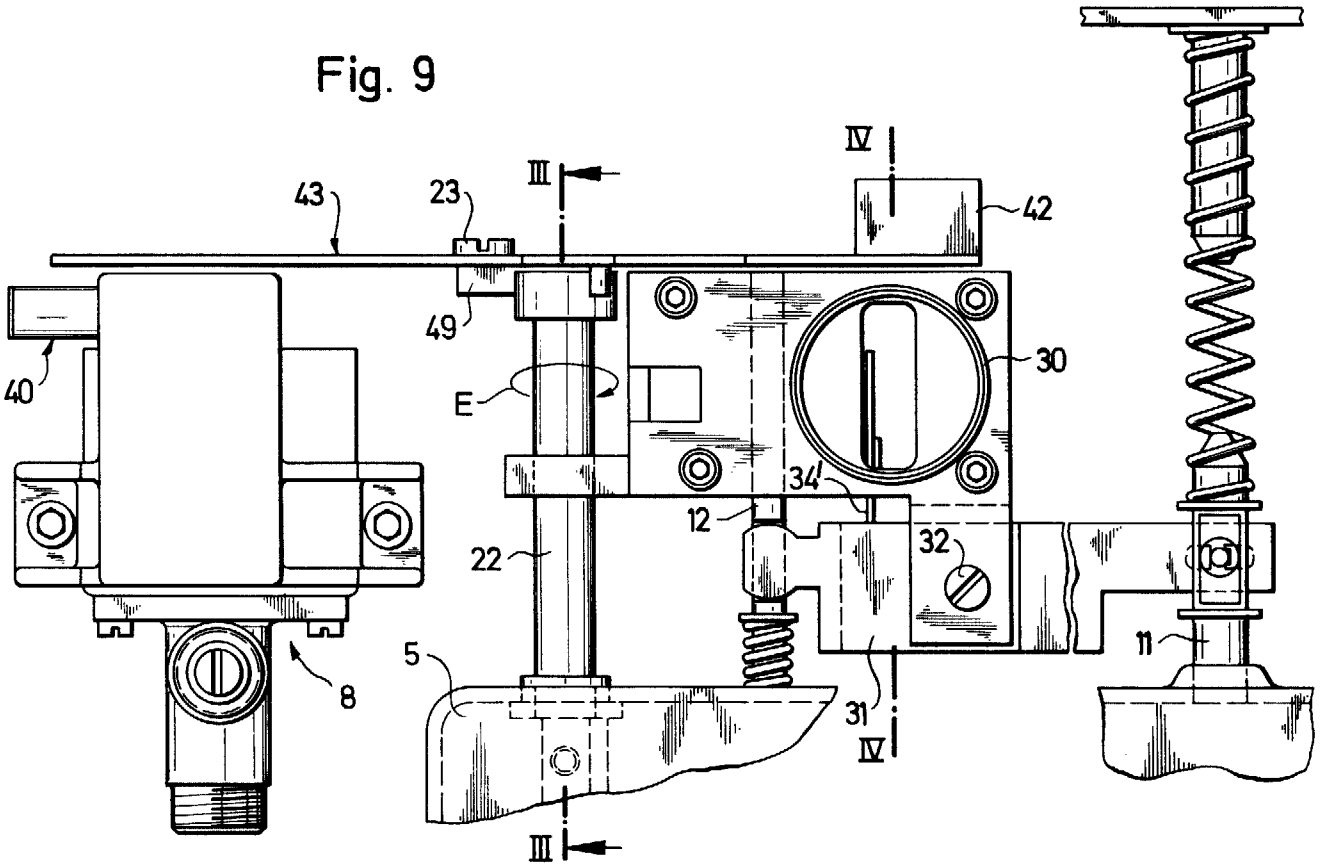
FIG. 9 is a view of the device of FIG. 8 taken in the direction of the arrow X.
Figure 10:
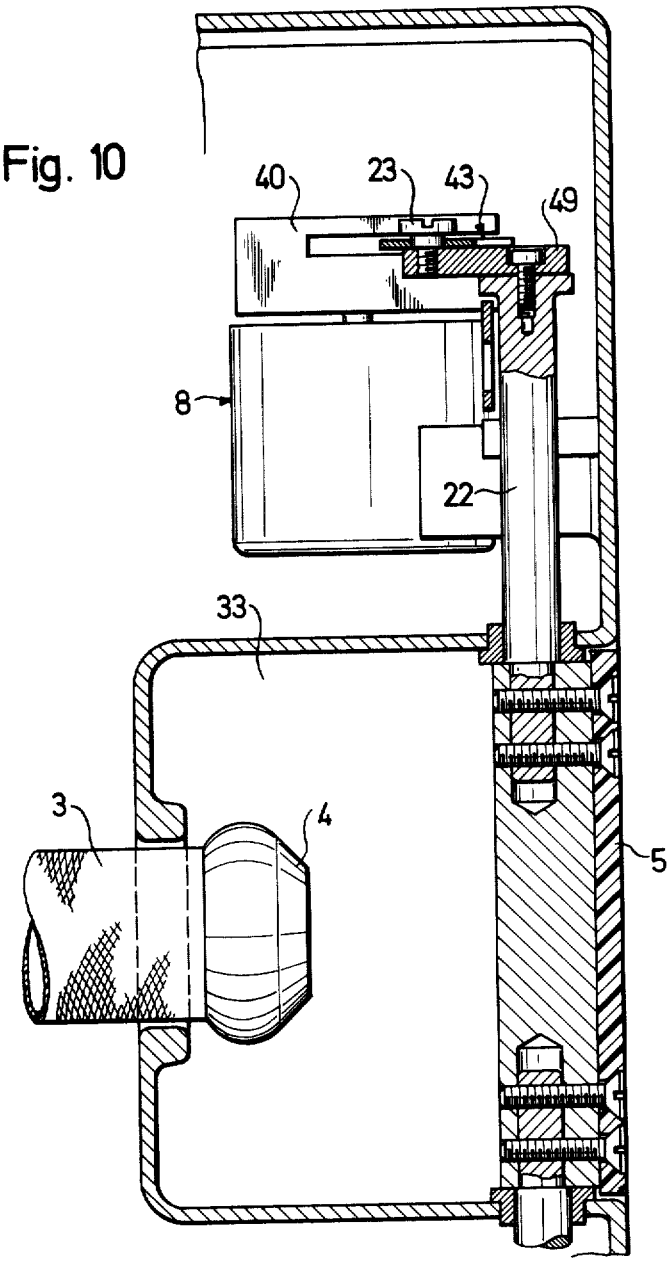
FIG. 10 is a section taken along the line III—III of FIG. 9.

After reduction of the storage pressure, the oxygen passes from the gas source within the housing via intermediate chambers into a flexible feed hose 3, at the end of which is an applicator 4 as shown in FIG. 10. For the inhalation of oxygen, a portion of the hose 3 is pulled out of the housing and the applicator 4 is held against the face in the region of mouth and nose. When the apparatus is not in use, the end of hose 3 with the applicator 4 is stored in the housing compartment 33 which is closed by the movable lid 5 and can be locked in the closed position by means of a locking bolt 11 as seen FIG. 9. When the lid 5 is moved into its open position, the oxygen shut-off valve 8 is opened and a short-duration timer 40 is actuated to shut the valve 8 after a predetermined time.

Figure 11:
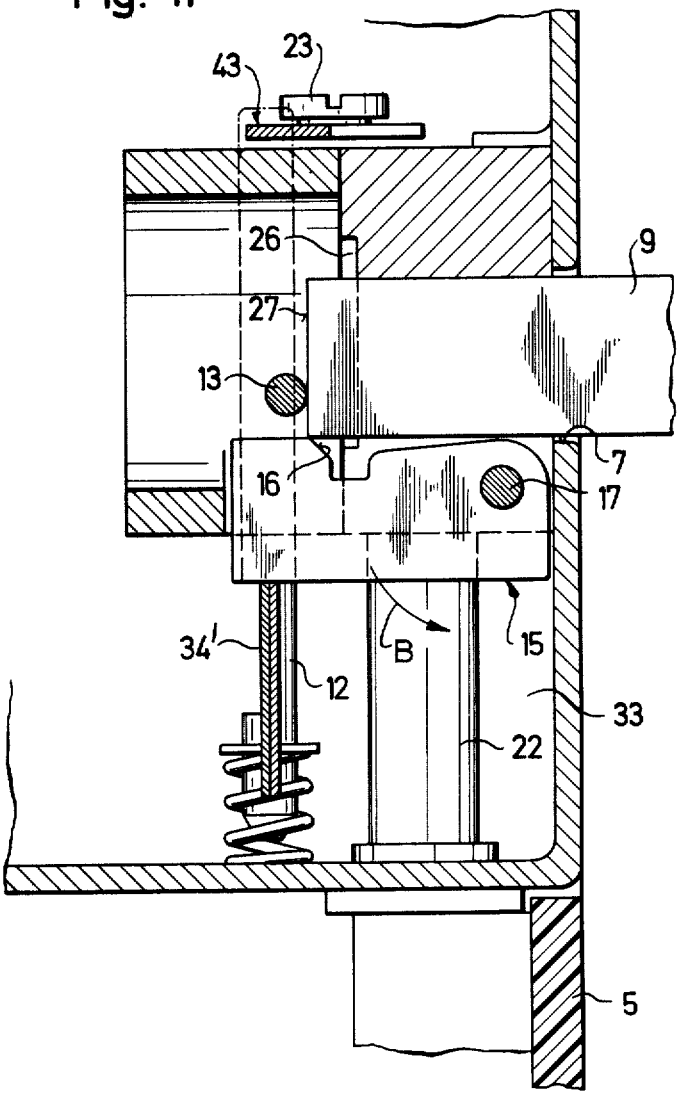
FIG. 11 is a section of the device of FIG. 9 taken along the line IV—IV.

An unlocking element 9 in FIG. 11 is pushed into the insertion slot formed by aperture 7 in housing 2. The strip preferably consists of a synthetic plastic material which can be configured to obviate imitations. The strip 9 causes the rocker arm 15 to be swivelled in the direction of the arrow B and to impinge upon lever arm 34 which in turn presses against lever 31 causing lever 31 to swivel around a bolt 32 as seen in FIG. 9. One end of the lever 31 cooperates with the locking bolt 11 to unlock lid 5 while the other end of lever 31 cooperates with the unlocking pin 12 which effects the swivelling position of the counter-poise 43.

Figure 8:
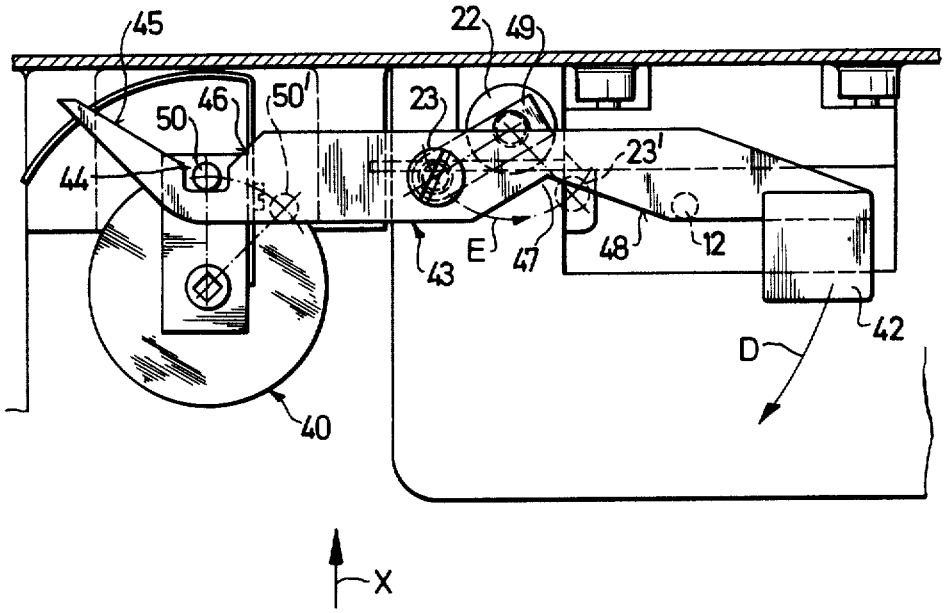
FIG. 8 is a side view of a further embodiment of the invention with the lid partially sectioned.

As soon as the unlocking pin 12 is moved in a downward direction as seen in FIG. 9 so that it no longer abuts the lower edge of the counter-poise 43, the counter-poise 43 swivels in the direction of the arrow D and assumes the position shown in FIG. 8. In this position, the winding bolt 50 of the timer 40 is moved into a rectangular groove 44 of the counter-poise 43.

The shaft 22 about which the lid 5 is swivelled includes a lug 49 which projects in radial direction and to which the counter-poise 43 is connected by a screw 23. The counter-poise 43 can thus easily pivot around the screw 23. Due to the weight 42 at one end of the counter-poise, the counter-poise 43 tends to rotate in the direction of the arrow D in FIG. 8.

The groove 44 in counter-poise 43 is bounded on either side by inclined abutting surfaces 45, 46 which define an angle of at least 90° to each other.

Between the axis of rotation of the counter-poise 43 and the weight 42 there is arranged on the underside of the counter-poise a triangular recess 47 having a guide edge 48 for the unlocking pin 12.

The apparatus of this third embodiment operates as follows: The unlocking element 9 is inserted into the recess 7 causing the locking bolt 11 to be unlocked, and the pin 12 to be retracted. When pin 12 retracts the counter-poise 43 which previously rested on the pin 12 will move under the influence of the weight 42 into the position shown in FIG. 8, in which the winding bolt 50 lies in the groove 44. The lid 5 can then be opened providing access to the hose 3 and attached applicator 4. Movement of the lid 5 causes a corresponding movement in shaft 22 and attached lug 49. Movement of lug 49 causes a motion of the screw 23 together with the attached counter-poise 43 in the direction of the arrow E in FIG. 8 so that the screw 23 and the winding bolt 50 then assume the positions 23' and 50' respectively. The motion of winding pin 50 causes the clockwork of the timer 40 to be wound and to start to run back towards the position shown as 50 in FIG. 8. During the return run the winding bolt 50 leaves the recess 44 in the counter-poise and moves along the abutting surface 45 and since the lid 5 remains open. The timer 40 is so designed that its actuating pin keeps the shut-off valve 8 in the open position during the time required for the winding pin 50 to return to its original position which may be, for example, 2 to 3 minutes. When the predetermined time has run out, the timer 40 closes the valve 8 in the oxygen supply conduit. When the unlocking element 9 has been withdrawn, the pin 12 passes into the region of the recess 47. When the end of the hose is then returned to the housing compartment 33 and the lid 5 is closed, the pin 12 moves along the guide edge 48 and holds the counter-poise in such a position that the winding bolt 50 cannot move into the groove 44. In this way, any misuse of the inhaler by partial closing and reopening of the lid is obviated.

Figure 12:
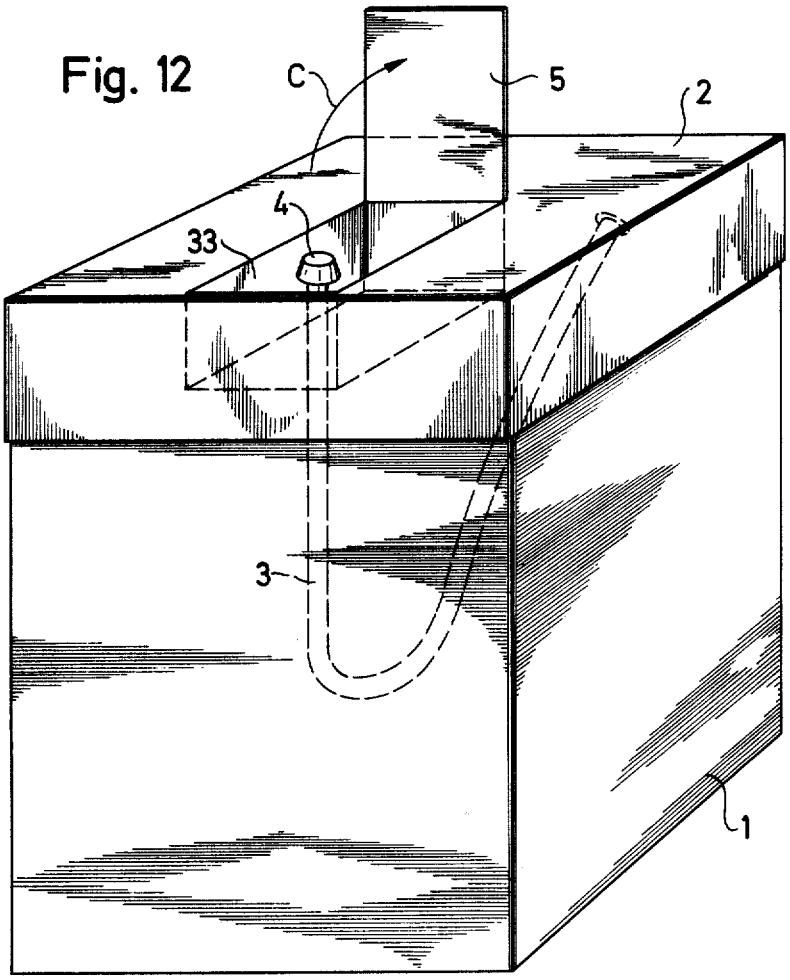
FIG. 12 is an isometric view of an inhaler with the lid opened.
Figure 13:
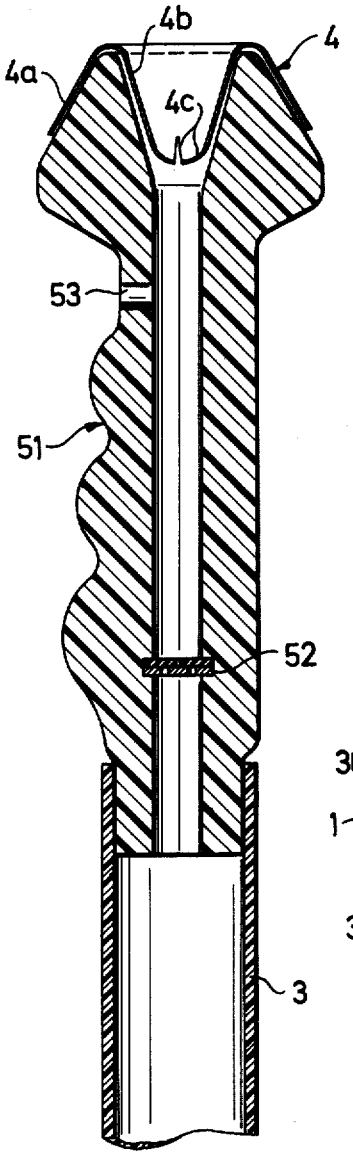
FIG. 13 is a section through the end of the feed hose showing the coupling organ and the applicator attached as inhaling mask.
Figure 14:
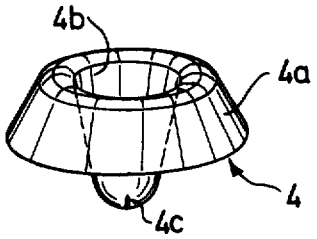
FIG. 14 is a perspective view of an inhaling mask designed as a disposable element.
Figure 15:
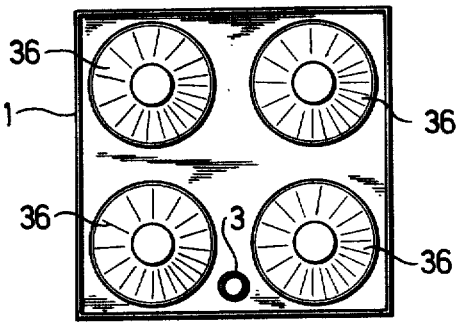
FIG. 15 is a diagrammatic illustration of the housing including gas sources.

The inhaler according to the embodiment shown in FIG. 12 approximately corresponds to that shown in FIG. 1 and comprises a housing 1, 2 the base of which accommodates four high-pressure gas cylinders as gas sources 36 in FIG. 15. These gas cylinders 36 are connected via connecting pipes to a pressure-reducing valve of conventional construction the outlet of which is connected to an expansion chamber which is not shown in detail in the drawing. A portion of the piece of the flexible feed hose 3 extends into the expansion chamber and is provided, as shown in FIG. 13, with a coupling member 51 designed as a handle and a holder. The lid 5 preferably consists of transparent material and acts to seal the housing compartment 33 wherein the coupling member 51 is stored. When the apparatus is not in use, the hose 3 extends in the form of a U- or V-shaped loop as seen in FIG. 12 into the interior of the housing 1, and this hose loop is located within the hollow space between the four gas cylinders or gas sources 36 which are arranged in the corners of the lower housing 1. For use, the coupling member 51 together with the end of hose 3 which is fixed to it can be pulled out of the housing compartment 33 and can be held with one hand against the region of mouth and nose. The hose 3 is long enough to reach the face of a tall standing person without compelling the person to bend down.

An applicator 4 is slipped onto the upper end of the coupling member 51 or alternatively directly onto the hose end. This applicator 4 may be easily removed and can be designed as a disposable component for reasons of hygiene. It can be connected to the coupling member 51 by simply slipping it into the recess in the end of the member according to FIG. 13. For this purpose, the applicator has a frustum-conical outer jacket 4a and a central portion 4b which is arched inwards to form a recess and is provided at the bottom of the recess with at least one perforation 4c which can be, for example, in the form of a cross-slot. This applicator 4 can be produced very economically from a synthetic plastic foil by the deep-drawing process.

The coupling member 51 is provided with a one-way valve 52 which prevents stale air from passing into the hose 3 during exhalation. Exhaled air exits through an outlet valve 53 opening laterally.

The expansion chamber which is now shown but is known from the prior art may contain substances based, for example, on menthol to flavour the gas flowing through the chamber. Prior to or instead of being aromatized, the gas can be moistened before it is passed into the hose 3. For the inhaling purposes of athletes, a suitable mixture of oxygen and other gases may be substituted for pure oxygen.

Figure 16:
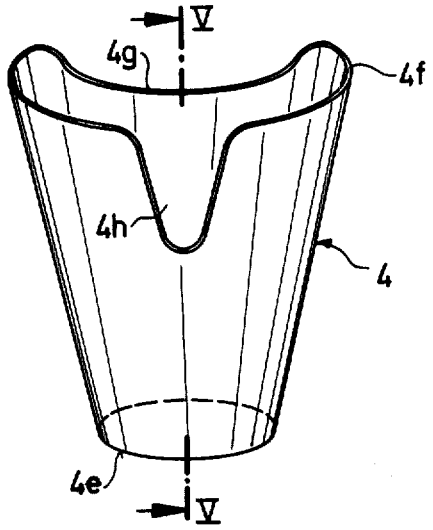
FIG. 16 is a perspective view of a first embodiment of the mask.
Figure 17:
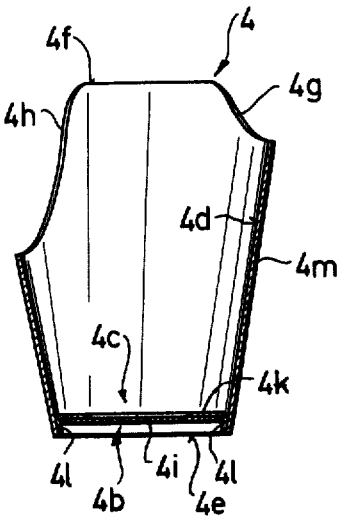
FIG. 17 is the part-section V—V of FIG. 16.
Figure 18:
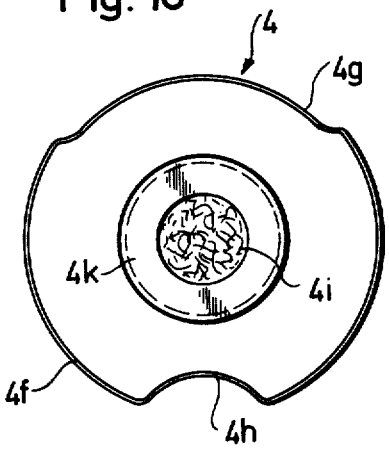
FIG. 18 is a plan view of the inhaling mask shown in FIG. 16.

The inhaling applicator illustrated in FIGS. 16 to 18 as a disposable element can be produced very economically without any sacrifice in operation. The inhaling applicator mask 4 consists of three parts, namely a conical cardboard sleeve 4m, a ring 4k inserted in the lower, narrowed part of sleeve 4m from which ring an outer flange 4l extends in axial direction with its lateral wall resting against the inner jacket of the cardboard sleeve 4m so that the lower edge 4e of the inhaling mask is at the same time reinforced by ring 4k and flange 4l and can be slipped onto the hose 3 or the coupling organ 51. A disc-shaped filter 4i is inserted in the small diameter end of sleeve 4m so that it covers the central perforation 4c but allows the gas to pass through. The filter 4i can consist of a staple fibre fleece which aborbs the breathing moisture of the inhaling person and prevents it from entering the hose. The ring 4k may consist of cardboard so that the whole inhaling mask is biodegradable and meets the demands of environment protection. At the end of the conical cardboard sleeve 4m having the greater diameter, there are two peripheral recesses 4g and 4h. The recess 4g extends in the form of an arch of about 120° over the periphery of the upper edge 4f of the conical sleeve 4m and during use rests against the chin of the user. The other recess 4h is narrower and only extends over an angle in segment of about 60° of the upper edge 4f. During use the recess 4h rests against the bridge of the nose of the user. The remaining parts of the upper edge 4f abut the cheeks of the user. Since this inhaling mask of FIGS. 16, 17 and 18 consists of a material which is rigid but elastically deformable, the end parts at the upper edge 4f and the recesses 4g and 4h which rest against the respective parts of the face of the user can form a virtual seal between the inhaling mask and the parts of the face of the user, including the nostrils and the mouth. No inhalant is therefore lost during inhaling.

Figure 19:
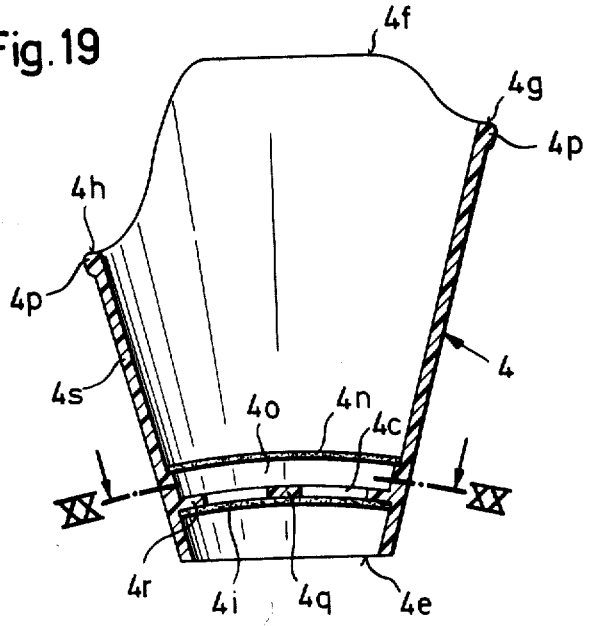
FIG. 19 is a sectional view of a second embodiment of an inhaling mask.

FIG. 19 shows an applicator having a generally frusto-conical side wall 4s, a top edge 4f and a lower edge 4e, the configuration of which follows generally that shown in the preceding applicator embodiment. Once again two recesses 4h and 4g are provided in the upper surface 4f to accommodate respectively the user's chin and nose. In this embodiment a raised ridge 4p extends around the periphery of the upper edge 4f. This rounded ridge 4p prevents a sharp edge which could cause lacerations and also strengthens the applicator along the surface which is pressed against the user's face.

Figure 20:
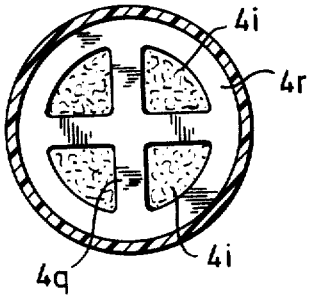
FIG. 20 is a sectional view taken along VI—VI of FIG. 19.

An annular flange 4( is attached to the inner surface of the side wall 4s at a point adjacent to its lower edge 4e. Cross members 4q extend outwardly from the flange 4r at right angles to each other so that they meet at the center of the disc-like opening defined by the flange 4r and divide the opening into four separate apertures 4c. A chamber 4o is formed between the partition formed by flange 4r and cross members 4q and a permeable wall 4n. A strip of filter material 4i which may, for instance, be made of a fleece material is disposed below the member composed of annular flange 4r and the cross members 4q. This layer of filter material extends across apertures 4c. Medication or aromatic substances may be placed in the chamber 4o. Also if desired, filter material 4i and/or the permeable wall 4n may be impregnated with materials to be inhaled. The embodiment showing in FIGS. 19 and 20 may advantageously be made of foamed plastic.

Figure 21:
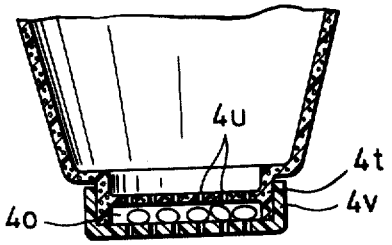
FIG. 21 is a sectional view of the lower end of a third embodiment of an inhaling mask.

FIG. 21 shows a sectional view of the base or smaller diameter end of a third embodiment of the applicator which embodiment is otherwise similar to that shown in FIG. 19. In this embodiment, which may for instance be made of polystyrene, the bottom portion 4t includes an annular indentation which forms a substantially cylindrical end portion. A disc-like portion 4z having a plurality of apertures 4u extends across the opening of bottom portion 4i. A cover member 4v is configured so that it fits over the cylindrical portion of 4t. The cover 4v includes a plurality of small apertures 4x which permit the passage of gas. Metered quantities of substances to be inhaled can be introduced into the chamber 4o formed between disc-like portion 4z of bottom portion 4t and cover 4v. These substances can be introduced easily since the cover 4v is removable. Preferably such substances, which may be medicines, are introduced on the surfaces of granular carrier materials having large surface areas.

I claim:

1. An inhaler apparatus comprises a housing and a breathing system mounted within said housing;

said breathing system includes a source of gas, an applicator for said gas, a feed hose connected between said source and said applicator, and valve means for controlling the flow of said gas to said applicator;

said housing includes a lid which is movable between an open position in which said applicator can be withdrawn from said housing and a closed position which prevents access to said applicator;

locking means to hold said lid in said closed position, and unlocking means to disengage said locking means;

timer means connected to said valve means for actuating said valve means for a predetermined period of time;

actuating means connected to said timer means for actuating said timer means; and connecting means connecting said lid and said timer means, said connecting means including a shaft fixedly connected to said lid; a first member fixedly connected to said shaft and extending radially outwardly therefrom, and first lever means connected between said first member and said actuating means whereby when said lid is moved into an open position said timer means actuates the valve means and thereby communicates the source with the applicator for said predetermined period time.

2. An inhaler as claimed in claim 1 including moistening means to moisten said gas said moistening means being arranged between said source and said applicator.

3. An inhaler apparatus according to claim 1 including mounting means connected to said housing said mounting means being adapted to support said applicator and at least a portion of said feed hose.

4. An inhaler according to claim 1 including a coupling member said coupling member being connected between said feed hose and said applicator and means to detachably connect said applicator to said coupling member.

5. An inhaler according to claim 4 in which said applicator includes a frusto conical outer wall having a larger and a smaller end, a wall member extending across said smaller end, said wall member having a substantially conical depression extending substantially along the axis of said frusto conical outer wall, said conical depression being configured to fit within said coupling member.

6. An inhaler according to claim 1 including a gas expansion chamber said gas expansion chamber being arranged between said gas source and said feed hose.

7. An inhaler according to claim 1 in which said applicator includes a frusto conical outer wall having a larger and a smaller end, said larger end having a first recess configured to fit over the chin of a person and a second recess substantially opposite said first recess which second recess is configured to fit over the bridge of the nose of a person, an annular member having at least one aperture attached to the inner surface of said wall at a point adjacent to and spaced from said smaller end and filter means extending across said at least one aperture in said annular member.

8. An inhaler as claimed in claim 7 in which said outer wall is made of a synthetic plastic material.

9. An inhaler as claimed in claim 7 in which said outer wall is made of a fibrous material.

10. An inhaler as claimed in claim 7 in which said filter means includes a layer of fiber fleece attached to said annular member and extending across said at least one aperture.

11. An inhaler as claimed in claim 7 in which said annular member includes a ring having a central aperture said ring extending inwardly from said outer wall and a cylindrical flange connected to said ring, said flange along the inner surface of said wall toward smaller end.

12. An inhaler as claimed in claim 7 in which said annular member includes a ring member attached to the inner surface of said wall and two substantially perpendicular strip members attached to said ring member and extending across said aperture in said ring member to divide said aperture into four smaller apertures, a disc-like member having a number of apertures said disc-like member being attached to the inner surface of said wall at a circle of points spaced from said annular member in a direction toward said large end of said wall to define a chamber between said disc-like member and said annular member.

13. An inhaler as claimed in claim 1 in which said applicator includes a substantially frustonconial wall member having a larger and a smaller end, said wall member including an annular recess at said small end and a substantially cylindrical wall portion extending outwardly from said recess to form a circular end, a first perforated disc-like member attached to the inner surface of said cylindrical wall portion, said first disc-like member being spaced from said circular end and a cover member configured to fit over the outer surface of said circular end of said cylindrical portion of said wall.

14. An inhaler as claimed in claim 13 in which said cover member includes a second disc-like member having a plurality of apertures and a diameter which is larger than the diameter of said cylindrical wall portion and a cylindrical flange extending outward from said second disc-like member said cylindrical flange being configured to slidably fit over the outer surface of said cylindrical wall portion said second disc-like member being spaced from said first disc-like member to define a chamber within said cylindrical wall portion which is suitable for the storage of medicines or aromatic substances.

15. An inhaler according to claim 1 in which said first member includes a disc connected to said shaft, and a pin mounted eccentrically on said disc, said first lever means being connected to said pin.

16. An inhaler apparatus as claimed in claim 1 in which said lid includes a recess, and said locking means includes a bolt movable into and out of engagement with said recess and in which said unlocking means includes a first rocker arm pivotably mounted on said housing and second lever means connecting said first rocker arm to said bolt to cause said bolt to move out of engagement with said recess in response to the pivoting of said first rocker arm and key means insertable into said housing to contact said first rocker arm causing said first rocker arm to pivot and said bolt to move out of engagement with said recess thereby permitting said lid to move from said closed to said open position.

17. An inhaler apparatus as claimed in claim 16 including means to render said key means unusable after a predetermined number of uses.

18. An inhaler apparatus as claimed in claim 16 in which said key means includes a relatively thin elongated member and in which such apparatus further includes cutting means which are activated in response to the motion of said lid from said closed to said open position to cut-off a portion of said thin elongated member.

19. An inhaler apparatus as claimed in claim 16 in which said second lever means includes a second member mounted adjacent to and movable by said first rocker arm and a second rocker arm having a first end adjacent to and movable by said second member and a second end, mounting means to pivotably mount said second rocker arm at a point between said first and second ends of said second rocker arm, said second end of said second rocker arm being connected to said bolt.

20. An inhaler apparatus as claimed in claim 16 including first biasing means to bias said bolt into said recess in said lid.

21. An inhaler apparatus according to claim 1 in which said first lever means includes a counter-poise having a first and second ends and a pivot point between said first and second ends, said first member of said connecting means being connected to said counter-poise at said pivot point and said counter-poise having a first recess adjacent to said first end which first recess cooperates with said actuating means, second biasing means to bias said counter-poise for motion in a predetermined direction about said pivot point, movable support means in contact with said counter-poise at a point between said pivot point and said second end to hold said counter-poise at a first predetermined orientation and thereby prevent motion in said predetermined direction, means responsive to said unlocking means to move said support means out of contact with said counter-poise and to permit said counter-poise to move in said predetermined direction about said pivot point to a second orientation in which said first recess has moved into engagement with said actuating means, and means including said connecting means and said first member to cause said counter-poise to move from said second orientation to a third orientation in response to the motion of said lid from said closed to said open position activating said timer for a predetermined period.

22. An inhaler apparatus as claimed in claim 21 in which said activating means includes a winding bolt and in which said first recess is formed in a first surface of said counter-poise and is configured to engage said winding bolt and said first recess includes at least a first sloping surface and in which said counter-poise has a second recess formed in a second surface which second recess includes at least a second sloping surface, said winding bolt being in contact with said first sloping surface and said support member being in contact with said second sloping surface while said counter-poise is moving from said third orientation to said first orientation under the influence of said second biasing means.

* * * * *